United States Patent
Cho et al.

(10) Patent No.: US 9,206,148 B2
(45) Date of Patent: Dec. 8, 2015

(54) METHOD FOR PRODUCING 5-HYDROXYMETHYL-2-FURFURAL FROM MAIZE SYRUP CONTAINING FRUCTOSE

(75) Inventors: Jin Ku Cho, Chungcheongnam-do (KR); Jaewon Jeong, Seoul (KR); Sangyong Kim, Chungcheongnam-do (KR); Bora Kim, Daejeon (KR); Baek-Jin Kim, Chungcheongnam-do (KR); Seunghan Shin, Seoul (KR); Dohoon Lee, Seoul (KR)

(73) Assignee: Korea Institute of Industrial Technology, Chungcheongnam-do (KR)

( * ) Notice: Subject to any disclaimer, the term of this patent is extended or adjusted under 35 U.S.C. 154(b) by 0 days.

(21) Appl. No.: 14/383,439

(22) PCT Filed: Jul. 26, 2012

(86) PCT No.: PCT/KR2012/005969
§ 371 (c)(1),
(2), (4) Date: Sep. 5, 2014

(87) PCT Pub. No.: WO2013/133489
PCT Pub. Date: Sep. 12, 2013

(65) Prior Publication Data
US 2015/0031904 A1    Jan. 29, 2015

(30) Foreign Application Priority Data
Mar. 5, 2012    (KR) .................. 10-2012-0022549

(51) Int. Cl.
C07D 307/50    (2006.01)
B01J 31/08    (2006.01)
C07D 307/48    (2006.01)

(52) U.S. Cl.
CPC .............. *C07D 307/50* (2013.01); *B01J 31/08* (2013.01); *C07D 307/48* (2013.01)

(58) Field of Classification Search
CPC ........................... C07D 307/48; C07D 307/50
See application file for complete search history.

(56) References Cited

U.S. PATENT DOCUMENTS

| 7,317,116 B2 * | 1/2008 | Sanborn ................ 549/483 |
| 2006/0142599 A1 | 6/2006 | Sanborn |
| 2009/0030215 A1 | 1/2009 | Dignan et al. |
| 2011/0071306 A1 | 3/2011 | Robinson |

FOREIGN PATENT DOCUMENTS

| EP | 2233476 A1 | 9/2010 |
| WO | WO 2013/053816 * | 4/2013 |

OTHER PUBLICATIONS

Szmant (J. Chem. Tech. Biotechnol. 1981, 31, 135-145).*
International Search Report in International Application No. PCT/KR2012/005969, filed Jul. 26, 2012.

* cited by examiner

*Primary Examiner* — Valerie Rodriguez-Garcia
(74) *Attorney, Agent, or Firm* — Saliwanchik, Lloyd & Eisenschenk

(57) ABSTRACT

Provided herein is a method for producing 5-hydroxymethyl-2-furfural (HMF) from maize syrup containing fructose including a conversion step in which a reaction product containing the 5-hydroxymethyl-2-furfural is produced by mixing and heating the maize syrup, a dioxane solvent and a solid acid catalyst, thus providing an advantage that the solvent can be easily isolated and the isolated solvent can be reused because dioxane is used as the solvent, and an advantage that the catalyst can be easily isolated and the isolated catalyst can be easily reused because a nonuniform solid acid catalyst is used.

15 Claims, 2 Drawing Sheets

METHOD FOR PRODUCING 5-HYDROXYMETHYL-2-FURFURAL FROM MAIZE SYRUP CONTAINING FRUCTOSE

CROSS-REFERENCE TO RELATED APPLICATIONS

This application is the U.S. national stage application of International Patent Application No. PCT/KR2012/005969, filed Jul. 26, 2012, which claims priority to Korean Application No. 10-2012-0022549, filed Mar. 5, 2012, the disclosures of each of which are incorporated herein by reference in their entirety.

BACKGROUND

1. Field

The following description relates to a method for producing 5-hydroxymethyl-2-furfural from maize syrup containing fructose, and more particularly, to a method for converting and purifying a raw material of maize syrup containing fructose that can be mass produced from carbohydrate biomass such as maize through a fermentation process, with an improved yield rate of 5-hydroxymethyl-2-furfural which is a core intermediate compound for biofuel and bioplastic, using a nonuniform solid acid catalyst having a dioxane solvent and an acid radical.

2. Description of Related Art

Oil demand is rapidly increasing due to the continuous decrease of oil reserves and growth of emerging & developing countries, causing imbalance of supply and demand in oil markets and leading to an era of high oil prices. Moreover, irreversible green house gases generated by reckless use of oil are causing serious environmental problems such as global warming.

Thus, the entire world is making efforts to replace oil resources with biomass resources that are replaceable and sustainable, for example, to mass produce commercial biofuels such as bioethanol and biodiesel, and bioplastic such as lactic acid and propanediol, to use them as transportation fuels and alternatives to petrochemicals.

As part of such efforts, 5-hydroxymethyl-2-furfural (HMF) which is a representative carbohydrate biomass-derived furan compound and a core intermediate compound for biofuel and bioplastic, is in the spotlight these days.

It is well known that 5-hydroxymethyl-2-furfural can be converted into 2,5-dimethylfuran (DMF) and 5-alkoxymethyl-2-furfural (AMF), and be used as the next generation biofuel. Furthermore, 5-hydroxymethyl-2-furfural has an energy density of gasoline level, and unlike bioethanols, it has a low hygroscopicity, thus there is no problem of corrosion even when stored for a long time. Not only that, unlike when producing bioethanol through an enzyme conversion process where 2 equivalents of carbon dioxide are inevitably discharged from 1 equivalent of hexose ($C_6H_{10}O_6 \rightarrow 2CH_3CH_2OH+2CO_2\uparrow$), the furan biofuels can be produced through a complete carbon-neutral process where there is no loss of carbon.

Furthermore, 5-hydroxymethyl-2-furfural can be converted into 2,5-furan dicarboxylic acid (FDCA), which is well known as an alternative to terephthalic acid (TPA), a monomer of PET. PET is produced through condensation polymerization using ethylene glycol (EG) and TPA as monomers, but while EG is under commercial production from bioethanol-based bioethylene to produce biomass-based PET, TPA is not being obtained from biomass yet.

Meanwhile, maize syrup containing fructose refers to high fructose maize syrup (HFCS), that has been under mass production since its manufacturing technology was first developed by Marshall in 1957 (R. O. Marshall, E. R. Kooi, Science, 1957, 125, 648), and is being widely used in food and beverage industries as an alternative to sugar. Maize syrup containing fructose is a mixture compound containing a large amount of fructose produced by converting maize that is a type of carbohydrate biomass, through a fermentation process. Furthermore, depending on the composition of fructose, HFCS may be classified into HFCS-90, HFCS-55, and HFCS-42 type HFCS that contains 90 parts by weight, 55 parts by weight, and 42 parts by weight, respectively. HFCS contains water and thus has a form of syrup.

Fructose which is the main substance of maize syrup containing fructose is well known to be converted into 5-hydroxymethyl-2-furfural when 3 water molecules are removed through a dehydration reaction. Recently, 5-hydroxymethyl-2-furfural is used as a core intermediate compound for biofuel and bioplastic, and so a lot of researches are being conducted for ways to mass produce 5-hydroxymethyl-2-furfural, but processes for commercially producing 5-hydroxymethyl-2-furfural have yet to be developed.

Most of the methods for converting fructose into 5-hydroxymethyl-2-furfural developed so far use dimethyl sulfoxide (DMSO) as solvent. That is because, by heating fructose under an acid condition, for 1 to 2 hours at 80 to 150° C. using DMSO as solvent, as much as 70 to 90% of the fructose can be converted into 5-hydroxymethyl-2-furfural. However, the boiling point of DMSO is very high, 189° C., and thus it is difficult to isolate DMSO through distillation. Not only that, DMSO can easily mix with most of other solvents, and thus there is also a disadvantage that it is difficult to recover 5-hydroxymethyl-2-furfural from DMSO through solvent extraction.

In order to solve the aforementioned problems, attempts have been made using DMSO with other solvents to conduct a conversion reaction in a binary system, in order to extract in real time the reactant product, 5-hydroxymethyl-2-furfural (G. W. Huber, J. N. Chheda, C. J. Barrett, J. A. Dumesic, Science 2005, 308, 1446), but there were limitations in extracting HMF completely from DMSO.

Therefore, to replace DMSO, DMF (N,N-dimethylformamide) which has a lower boiling point (G. A. Halliday, R. J. Young, V. V. Grushin, Org. Lett. 2003, 5, 2003) or ionic liquids from which a reactant product can be extracted easily (H. B. Zhao, J. E. Holladay, H. Brown, Z. C. Zhang, Science, 2007, 316, 1597) were used. However, the boiling point of DMF is still high (153° C.), and so are the prices of ionic liquids, and thus they are not economically feasible to be applied to commercial mass production.

SUMMARY

Therefore, a purpose of an embodiment of the present invention is to resolve the aforementioned problems of prior art, that is to provide a method for converting maize syrup containing fructose into 5-hydroxymethyl-2-furfural with an excellent yield rate.

Therefore, a purpose of an embodiment of the present invention is to resolve the aforementioned problems of prior art, that is to provide a method for converting maize syrup containing fructose into 5-hydroxymethyl-2-furfural with an excellent yield rate.

Another purpose of an embodiment of the present invention is to provide a method for converting maize syrup containing fructose into 5-hydroxymethyl-2-furfural wherein the dioxane, nonuniform solid acid catalyst and organic solvent can be reused, so that such a reaction can be performed continuously, thus enabling commercial mass production of 5-hydroxymethyl-2-furfural.

According to an embodiment of the present invention, there is provided a method for producing 5-hydroxymethyl-2-furfural (HMF) from maize syrup containing fructose, wherein the 5-hydroxymethyl-2-furfural is expressed by chemical formula:

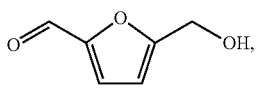

and the method comprises a conversion step in which a reactant containing the 5-hydroxymethyl-2-furfural is produced by mixing and heating the maize syrup, a dioxane solvent, and a solid acid catalyst (S10).

The method may further include a filtration step of filtering the solid acid catalyst from the reactant (S20); a distillation step of distilling the dioxane from the reactant that underwent the filtration step (S30); a purification step of purifying the reactant that underwent the distillation step (S40); and a recovery step of recovering organic solvent from the reactant that underwent the purification step (S50).

At the conversion step (S10), the maize syrup may include water, and carbohydrate including the fructose.

The maize syrup may include 20 to 30 parts by weight of water for 100 parts by weight of carbohydrate. purification step (S50).

More specifically, the maize syrup may include 40 to 95 parts by equivalent of fructose for 100 parts by equivalent of carbohydrate. And the maize syrup may be generated by an isomerization reaction under pH of 4 to 9. At the conversion step (S10), the maize syrup may constitute 1 to 50 parts by weight for 100 parts by weight of dioxane.

At the conversion step (S10), the solid acid catalyst may be a cation exchange resin. The solid acid catalyst may have a form of a Bronsted acid or Lewis acid functional radical connected on an organic or inorganic support. The solid acid catalyst may include 0.1 to 1 parts by equivalent of acid radical of the Bronsted acid or Lewis acid functional radical for 100 parts by equivalent of the fructose.

At the conversion step (S10), conversion may be performed at a temperature of 80 to 150° C., and conversion may take 1 to 8 hours.

At the filtration step (S20), the isolated solid acid catalyst may be reused as catalyst at the conversion step (S10). At the distillation step (S30), the isolated dioxane may be reused as solvent at the conversion step (S10).

At the purification step (S40), the reactant that underwent the distillation step may be separated into an organic solvent layer comprising the 5-hydroxymethyl-2-furfural and a water layer comprising byproducts, by adding organic solvent and water to the reactant.

At the recovery step (S50), the organic solvent layer may be dried through a dehydration process and the organic solvent may be distilled, and thus the 5-hydroxymethyl-2-furfural may be obtained.

At the recovery step (S50), the isolated organic solvent may be reused at the purification step (S40).

The aforementioned embodiments of the present invention provide an effect of efficiently mass producing 5-hydroxymethyl-2-furfural, that is a core intermediate compound for biofuel and bioplastic.

Furthermore, the aforementioned embodiments of the present invention provide an effect of directly using, as raw material, maize syrup containing fructose that is under commercial mass production, thus maximizing economic feasibility in terms of raw material costs.

Furthermore, the aforementioned embodiments of the present invention also provide an effect of using dioxane as solvent, and nonuniform solid acid catalyst as catalyst, which are both easily separable and reusable.

Furthermore, the aforementioned embodiments of the present invention also provide an effect of removing byproducts in the reactant using an organic solvent and water, thereby easily purifying 5-hydroxylmethyl-2-furfural, and also an effect of separating the used organic solvent at the purification step by distillation and reusing it.

BRIEF DESCRIPTION OF THE DRAWINGS

Throughout the drawings and the detailed description, unless otherwise described, the same drawing reference numerals will be understood to refer to the same elements, features, and structures. The relative size and depiction of these elements may be exaggerated for clarity, illustrating, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

Figure 1:
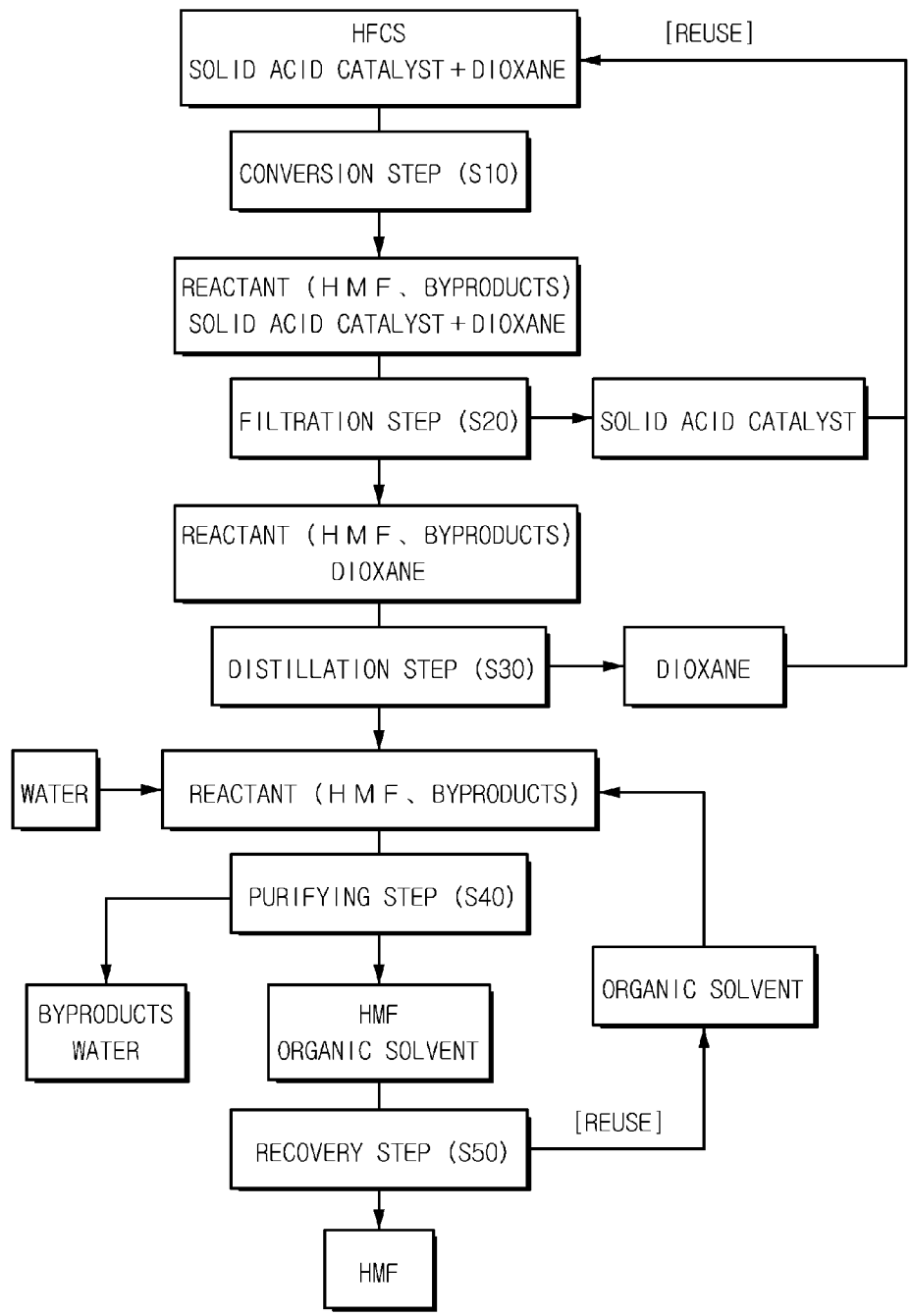
FIG. 1 is a flowchart sequentially illustrating a method for producing 5-hydroxymethyl-2-furfural (HMF) from maize syrup containing fructose according to an embodiment of the present invention.

Hereinafter, a method for producing 5-hydroxymethyl-2-furfural (HMF) from maize syrup containing fructose according to an embodiment of the present invention will be explained in detail with reference to FIG. 1.

First of all, in the method for producing 5-hydroxymethyl-2-furfural (HMF) from maize syrup containing fructose according to an embodiment of the present invention, the 5-hydroxymethyl-2-furfural is expressed in the chemical formula shown below:

[Chemical formula]

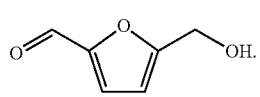

And the method for producing 5-hydroxymethyl-2-furfural (HMF) from maize syrup containing fructose according to an embodiment of the present invention includes a conversion step wherein a reactant including the 5-hydroxymethyl-2-furfural is produced by mixing and heating the maize syrup, a dioxane solvent, and a solid acid catalyst (S10).

At the conversion step (S10), the maize syrup is one that includes carbohydrate that includes fructose, and water, and the maize syrup includes 20 to 30 parts by weight of water for every 100 parts by weight of carbohydrate, thus having a form of syrup. However, even if the water is outside the range of 20 to 30 parts by weight for every 100 parts by weight of carbohydrate, there is no effect to the yield rate.

Herein, the fructose may be desirably 40 to 95 parts by equivalent for 100 parts by equivalent of carbohydrate, and more desirably 60 to 95 parts by equivalent. The fructose being less than 40 parts by equivalent for 100 parts by equivalent of carbohydrate doesn't affect the yield rate, but the total yield rate of the 5-hydroxymethyl-2-furfural converted from the fructose will decrease proportionately, thus the fructose being less than 40 parts by equivalent for 100 parts by equivalent of carbohydrate is not appropriate in terms of economic feasibility. The fructose exceeding 95 parts by equivalent for 100 parts by equivalent of carbohydrate doesn't affect the yield rate either, but the total yield rate of the 5-hydroxymethyl-2-furfural converted from the fructose will increase proportionately. However, it is difficult to find a maize syrup that contains fructose exceeding 95 parts by equivalent from the maize syrups generally available on the market at low prices. An additional process is required to obtain a maize syrup containing more than 95 parts by equivalent of fructose for 100 parts by equivalent of carbohydrate, and thus it is not desirable in terms of economic feasibility.

The maize syrup is generated by isomerization under the condition of pH of 4 to 9, more desirably pH of 6 to 8. pH of less than 4 or pH of above 9 is outside the general conditions for the reaction of an isomerizase, and thus, under such conditions, isomerization will not occur, and maize syrup will not be generated.

Furthermore, at the conversion step (S10), the maize syrup is desirably 1 to 50 parts by weight for 100 parts by weight of the dioxane, more desirably, 10 to 30 parts by weight for 100 parts by weight of the dioxane. According to numerous experiments results, using maize syrup of less than 1 parts by weight requires much energy to be consumed for distilling and separating dioxane, thus increasing the processing cost, whereas using maize syrup that exceeds 50 parts by weight will delay the reacting time and reduce the conversion efficiency.

At the conversion step (S10), the solid acid catalyst may be desirably a cation exchange resin, and the solid acid catalyst may be desirably an organic or inorganic support connected with a Bronsted acid or Lewis acid functional radical.

More specifically, the organic support may be a high molecular support having at least one of polystyrene, polyamide, and polyethyleneglicol, and the inorganic support may be an inorganic compound having at least one of silica, alumina, zeolite, and carbon. And the acid radical chemically connected on such a support may be desirably a Bronsted acid or a Lewis acid through a metal coordinated to a ligand.

Furthermore, 0.1 to 1 parts by equivalent, more desirably 0.4 to 0.7 parts by equivalent of acid radical of the Bronsted acid or Lewis acid may be used for 100 parts by equivalent of fructose. The acid radical used in the solid acid catalyst being less than 0.1 parts by equivalent for 100 parts by equivalent of the fructose of maize syrup has a disadvantage of reducing the conversion efficiency, whereas the acid radical used in the solid acid catalyst being above 1 parts by equivalent for 100 parts by equivalent of the fructose of maize syrup has a disadvantage of increasing the purchasing costs of the solid acid catalyst, and increasing the processing costs necessary for filtering and washing the solid acid catalyst when reusing it.

At the conversion step (S10), the heating temperature may be 70 to 180° C., more desirably 80 to 150° C. The heating temperature being less than 70° C. has a problem of delaying the reacting speed, and the heating temperature being above 180° C. has a problem of increasing generation of byproducts.

At the conversion step (S10), the heating time may be 30 minutes to 15 hours, more desirably 1 hour to 8 hours, to obtain 5-hydroxymethyl-2-furfural, that is the target substance, with the highest yield rate. More specifically, the heating time being less than 30 minutes has a disadvantage of reducing the conversion efficiency, and the heating time exceeding 15 hours has a problem of increasing generation of byproducts.

Furthermore, the method for producing 5-hydroxymethyl-2-furfural (HMF) from maize syrup containing fructose according to an embodiment of the present invention further includes a filtration step of filtering the solid acid catalyst from the reactant (S20), a distillation step of distilling the dioxane from the reactant that underwent the filtration step (S30), a purification step of removing byproducts and water from the reactant that underwent the distillation step (S40), and a recovery step of recovering organic solvent from the reactant that underwent the purification step (S50).

At the filtration step (S20), the isolated solid acid catalyst may be desirably reused as a catalyst at the conversion step (S10), and at the distillation step (S30), the isolated dioxane may be desirably reused as a solvent at the conversion step (S10).

At the filtration step (S20), the solid acid catalyst can be easily isolated from the liquid reactant, and can be reused. Isolation between the solid acid catalyst and the liquid reactant is made using the difference of density between the solid acid catalyst and the liquid reactant. Due to the difference of density, when stored for a certain period of time, the solid catalyst will be precipitated on the bottom of the reactor, enabling easy isolation of the liquid reactant. Accordingly, the liquid product and the solid acid catalyst can be easily isolated from each other using generally used filtering devices or filtering paper.

At the filtration step (S20), the solid acid catalyst may be reused at the conversion step (S10). The solid acid catalyst that underwent the filtration step (S20) may be washed and reactivated by washing the solid acid catalyst with acetone for desirably 1 to 4 times, more desirably 2 to 3 times, and then washing the solid acid catalyst with distilled water for desirably 1 to 4 times, more desirably 2 to 3 times, and then processing the solid acid catalyst with hydrochloric acid for desirably 1 to 4 times, more desirably 2 to 3 times, and then with distilled water for 1 to 4 times, more desirably 2 to 3 times, and then with acetonitrile for desirably 1 to 4 times, more desirably 2 to 3 times. Then, after going through a drying process, the solid acid catalyst may be reused at the conversion step (S10).

At the distillation step (S30), compared to conventional methods where a DMSO solvent having a boiling point of 189° C. (at 750 mmHg) is used to obtain 5-hydroxymethyl-2-furfural, in an embodiment of the present invention, the boiling point of the dioxane solvent is 95 to 105° C. (at 750 mmHg), and thus distillation can be made relatively more easily and separation can be made easily using any device based on the boiling point within the aforementioned range. Isolated dioxane has an advantage to be reused as solvent at the conversion step (S10).

At the purification step (S40), when an organic solvent and water are added to the reactant that underwent the distillation step (S30), the reactant is effectively separated into an organic solvent layer containing the 5-hydroxymethyl-2-furfural and a water layer containing byproducts. Therefore, organic solvent used herein may desirably be one that can dissolve 5-hydroxymethyl-2-furfural but that does not mix with water. The organic solvent may be desirably at least one of ethyl acetate (EA), diethyl ether, dichloromethane, chloroform, and methyl isobutyl ketone (MIBK).

At the recovery step (S50), the organic solvent layer is dried through a dehydration process, and the organic solvent is distilled, and thus 5-hydroxymethyl-2-furfural is obtained. Furthermore, at the recovery step (S50), the isolated organic solvent may be reused at the purification step (S40).

Hereinabove, the method for producing 5-hydroxymethyl-2-furfural from maize syrup containing fructose according to an embodiment of the present invention was explained by individually explaining the conversion step (S10), filtration step (S20), distillation step (S30), purification step (S40), and recovery step (S50).

That is, 5-hydroxymethyl-2-furfural is produced from maize syrup containing fructose in the method including the conversion step wherein a reactant including the 5-hydroxymethyl-2-furfural is provided by mixing and heating maize syrup that includes the fructose (HFCS) as starting material, dioxane, and solid acid catalyst (S10), the method further including the filtration step of filtering the solid acid catalyst from the reactant, the distillation step of distilling the dioxane from the reactant that underwent the filtration step, the purification step of removing byproducts and water from the reactant that underwent the distillation step, and the recovery step of recovering organic solvent from the reactant the underwent the purification step.

Hereinafter, there will be explained experiment results for proving the excellence of the method for producing 5-hydroxymethyl-2-furfural from maize syrup containing fructose according to an embodiment of the present invention.

In experiment example 1, in order to select the optimal solvent to be used for converting maize syrup containing fructose into 5-hydroxymethyl-2-furfural, different yield rates of 5-hydroxymethyl-2-furfural were compared obtained from applying different organic solvents. Accordingly, dioxane was selected as the optimal solvent.

Furthermore, in experiment example 2, in order to obtain the optimal reacting time, different yield rates of 5-hydroxymethyl-2-furfural were compared obtained from applying different reacting times. In experiment example 3, different yield rates of 5-hydroxymethyl-2-furfural were compared obtained from applying different amounts of acid radical in the solid acid catalyst, and in experiment example 4, different yield rates of 5-hydroxymethyl-2-furfural were compared obtained from applying different concentrations of maize syrup containing fructose.

Furthermore, in experiment example 5, different yield rates of 5-hydroxymethyl-2-furfural were compared obtained from applying different number of times of reusing the catalyst, and in experiment 6, 5-hydroxymethyl-2-furfural was produced from maize syrup containing fructose in the overall method of the present disclosure.

<Forms for Implementation of the Present Disclosure>

The present disclosure will be well understood by the following experiment examples which are for exemplary purpose only, and not for limiting the scope of protection specified by the claims.

Application of Experiment Example 1 Solvent

High-fructose maize syrup (HFCS) was put into a plurality of tubular type reactors, by 430 mg each (containing 300 mg of carbohydrate wherein fructose is 270 mg, 1.5 mmol). Next, Amberlyst 15 resin (Aldrich, 4.7 meq of H+/g resin) wherein a sulfonic acid radical is connected to a polystyrene support was put into the reactors, by 300 mg each (wherein Bronsted acid radical in the solid acid catalyst was 1.4 mmol). Next, 3 mL of dimethylformamide (DMF), acetonitrile, dioxane, isopropanol, dimethylhydrofuran (THF), and dimethylsulfoxide (DMSO) were put into each reactor, and then reaction was proceeded by stirring for 4 hours while raising the temperature up to 100° C.

After the reaction, the temperature was turned down to room temperature, and then after diluting the reactant with HPLC grade distilled water, an HPLC analysis was conducted to measure the yield rates. Specimens were isolated by ion-exclusion column (Bio-Rad Aminex HPX-87H 3007.8 mm) on a high performance liquid chromatography (Agilent 1200 series), and then the yield rates of the generated 5-hydroxymethyl-2-furfural (HMF) were measured by an RID detector.

As a result of the HPLC analysis, the yield rates of 5-hydroxymethyl-2-furfural (HMF) for each solvent under the aforementioned reaction conditions were as shown in table 1. It can be seen that the yield rate was 79% or more when dioxane was used as solvent. This is an excellent result that is close to the 81% or more yield rate of 5-hydroxymethyl-2-furfural (HMF) obtained when using dimethylsulfoxide (DMSO), well known as the optimal solvent in conventional methods.

TABLE 1

Yield rates of 5-hydroxymethyl-2-furfural according to organic solvent (temperature 100° C.)

| Number of order | Organic solvent | Metal catalyst | Temperature (° C.) | Time (hr) | HMF Yield rate (%) |
|---|---|---|---|---|---|
| 1 | Dimethylformamide (DMF) | Amberlyst 15 | 100 | 4 | 66 |
| 2 | Acetonitrile | Amberlyst 15 | 100 | 4 | 44 |
| 3 | Dioxane | Amberlyst 15 | 100 | 4 | 79 |
| 4 | Isopropanol | Amberlyst 15 | 100 | 4 | 51 |
| 5 | Tetrahydrofuran (THF) | Amberlyst 15 | 100 | 4 | 25 |
| 6 | dimethylsulfoxide | Amberlyst 15 | 100 | 4 | 81 |

Experiment Example 2

Optimization of Reaction Time 14.3 g of high-fructose maize syrup (HFCS) (containing 10 g of carbohydrate wherein fructose is 9 g, 50 mmol) was put into a 250 mL round-bottom flask. Next, 10 g of Amberlyst 15 resin where a sulfonic acid radical is connected to a polystyrene support was added. Next, 100 mL of dioxane was put into the reactor, and then specimens were taken after different periods of time while raising the temperature up to 100° C. Then, the fructose being consumed and the yield rate of 5-hydroxymethyl-2-furfural (HMF) were measured through an HPLC analysis. As a result of the HPLC analysis, the yield rates of 5-hydroxymethyl-2-furfural (HMF) according to different reacting times were as shown in table 2.

It can be seen that the yield rate of 5-hydroxymethyl-2-furfural was the highest when reacted for 3 hours, and that after 3 hours, generation of byproducts such as levulinic acid increased and the yield rate of 5-hydroxymethyl-2-furfural gradually decreased.

TABLE 2

Experiment example 3: Yield rates of 5-hydroxymethyl-2-furfural according to reacting time (temperature 100° C.)

| Number of order | Organic solvent | Metal catalyst | Temperature ° C. | Time (hr) | HMF Yield rate (%) |
|---|---|---|---|---|---|
| 1 | Dioxane | Amberlyst 15 | 100 | 0.5 | 21 |
| 2 | Dioxane | Amberlyst 15 | 100 | 1 | 55 |
| 3 | Dioxane | Amberlyst 15 | 100 | 2 | 74 |
| 4 | Dioxane | Amberlyst 15 | 100 | 3 | 80 |
| 5 | Dioxane | Amberlyst 15 | 100 | 4 | 77 |
| 6 | Dioxane | Amberlyst 15 | 100 | 5 | 75 |
| 7 | Dioxane | Amberlyst 15 | 100 | 6 | 74 |
| 8 | Dioxane | Amberlyst 15 | 100 | 20 | 43 |

Experimental Example 3

Effects According to Different Amounts of Acid Radicals in Solid Acid Catalyst

Amberlyst 15 resin (4.7 meq of H+/g resin) was put into a plurality of reactors by different amounts of 10 g, 5 g, 2 g, and 1 g, in order to observe the effects of reaction according to different amounts of acid radicals in the solid acid catalyst. Next, 14.3 g of high-fructose maize syrup (HFCS) (fructose 9 g) and 100 mL of dioxane were put into each reactor, and then reaction was proceeded by stirring while raising the temperature up to 100° C. After the reaction, the yield rates of the 5-hydroxymethyl-2-furfural (HMF) generated were measured through an HPLC analysis. As a result of the HPLC analysis, the yield rates of 5-hydroxymethyl-2-furfural according to different amounts of acid radicals inside the solid acid catalyst were as shown in table 3.

According to the experiment, when the amount of solid acid catalyst decreases, the reacting time is delayed, but even with only 2 g of Amberlyst 15 resin (acid radicals inside the solid acid catalyst/fructose=0.19), almost 70% of yield rate of 5-hydroxymethyl-2-furfural could be obtained.

TABLE 3

Yield rates of 5-hydroxymethyl-2-furfural (HMF) according to amounts of acid radicals in solid acid catalyst

| Number of order | Organic solvent | Solid acid catalyst | Amount of solid acid catalyst (g) | Parts by equivalent of acid radicals/ fructose | Temperature ° C. | Time (hr) | HMF Yield rate (%) |
| --- | --- | --- | --- | --- | --- | --- | --- |
| 1 | Dioxane | Amberlyst 15 | 10 | 0.94 | 100 | 3 | 80 |
| 2 | Dioxane | Amberlyst 15 | 5 | 0.46 | 100 | 5 | 74 |
| 3 | Dioxane | Amberlyst 15 | 2 | 0.19 | 100 | 7 | 68 |
| 4 | Dioxane | Amberlyst 15 | 1 | 0.09 | 100 | 7 | 49 |

Experiment Example 4

Yield Rates of 5-Hydroxymethyl-2-Furfural (HMF) According to Concentration of High-Fructose Maize Syrup In order to observe the effects of reaction according to different concentrations of high-fructose maize syrup (HFCS), different amounts of high-fructose maize syrup: 14.3 (fructose 9 g), 28.6 g (fructose 18 g), 42.9 g (fructose 27 g), 71.9 g (fructose 45 g) were put into each reactor. Next, 10 g of Amberlyst 15 resin and 100 mL of dioxane were added to each reactor, and reaction was proceeded by stirring while raising the temperature up to 100° C. Then, the yield rates of 5-hydroxymethyl-2-furfural (HMF) were measured through an HPLC analysis.

As a result of the HPLC analysis, the yield rates of 5-hydroxymethyl-2-furfural (HMF) according to different concentrations of high-fructose maize syrup (HFCS) were as shown in table 4. According to the experiment, it was found that when the concentration of the high-fructose maize syrup (HFCS) increases, the reacting time is delayed, but even under a reaction condition of high concentration (concentration of fructose in the high-fructose maize syrup: 1.5M) where 42.9 g of high-fructose maize syrup (HFCS) was put into 100 mL of dioxane, almost 60% or more yield rate of 5-hydroxymethyl-2-furfural could be obtained within 7 hours.

Experiment Example 5

Reuse of Solid Acid Catalyst 14.3 g of high-fructose maize syrup (containing 10 g of carbohydrate, wherein fructose is 9 g, 50 mmol) was put into a 250 mL round-bottom flask, and 10 g of Amberlyst 15 resin was added therein. Next, 100 mL of dioxane was put into the reactor, and stirred for 3 hours at 100° C. After the reaction, Amberlyst 15 was filtered, and then the reactant was washed and reactivated by processing with acetone for 3 times, with distilled water for 3 times, with 2N NaOH for 2 times, with distilled water for 2 times, with 3N HCl for 2 times, with distilled water for 2 times, and with acetonitrile for 2 times. Then, the reactant was dried and reused for the next reaction. As a result of the HPLC analysis on the yield rates of 5-hydroxymethyl-2-furfural obtained by reusing Amberlyst 15 resin, it could be seen that the activity of Amberlyst 15 was sustainable.

TABLE 5

Yield rates of 5-hydroxymethyl-2-furfural (HMF) according to number of times of reusing solid acid catalyst

| Number of order | Organic solvent | Solid acid catalyst | Temperature (° C.) | Time (hr) | Number of times of reuse (times) | HMF Yield rate (%) |
| --- | --- | --- | --- | --- | --- | --- |
| 1 | Dioxane | Amberlyst 15 | 100 | 3 | 1 | 79 |
| 2 | Dioxane | Amberlyst 15 | 100 | 3 | 2 | 77 |
| 3 | Dioxane | Amberlyst 15 | 100 | 3 | 3 | 80 |
| 4 | Dioxane | Amberlyst 15 | 100 | 3 | 4 | 81 |
| 5 | Dioxane | Amberlyst 15 | 100 | 3 | 5 | 82 |

TABLE 4

Yield rates of 5-hydroxymethyl-2-furfural (HMF) according to concentration of high-fructose maize syrup

| Number of order | Organic solvent | Solid acid catalyst | Amount high-fructose maize syrup (g) | Concentration of fructose in the high-fructose maize syrup (M) | Temperature (° C.) | Time (hr) | HMF Yield rate (%) |
| --- | --- | --- | --- | --- | --- | --- | --- |
| 1 | Dioxane | Amberlyst 15 | 14.3 | 0.5 | 100 | 3 | 80 |
| 2 | Dioxane | Amberlyst 15 | 28.6 | 1 | 100 | 5 | 66 |
| 3 | Dioxane | Amberlyst 15 | 42.9 | 1.5 | 100 | 7 | 61 |
| 4 | Dioxane | Amberlyst 15 | 71.5 | 2.5 | 100 | 7 | 35 |

Experiment Example 6

Producing 5-Hydroxymethyl-2-Furfural (HMF)

Figure 2:
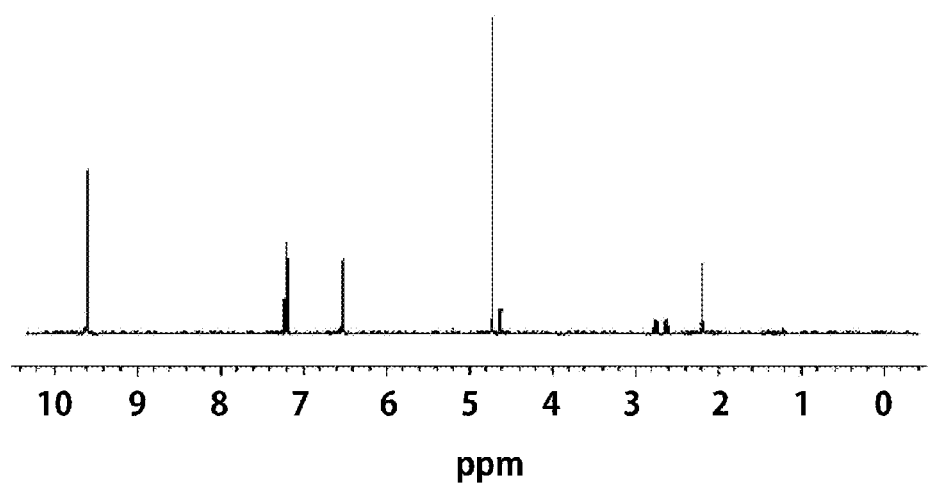
FIG. 2 is a 1H-NMR result graph of HMF obtained from a method for producing 5-hydroxymethyl-2-furfural (HMF) from maize syrup containing fructose according to an embodiment of the present invention.

14.3 g of high-fructose maize syrup (containing 10 g of carbohydrate, wherein fructose is 9 g, 50 mmol) was put into a 250 mL round-bottom flask, and 10 g of Amberlyst 15 resin was added therein. Next, 100 mL of dioxane was put into the reactor, and stirred for 3 hours at 100° C. After the reaction, Amberlyst 15 resin was filtered and removed, and the dioxane was distilled and thus to obtain a reactant compound. Ethyl acetate (100 mL) and distilled water (100 mL) were put into the obtained reactant compound. After conducting a delamination, the ethyl acetate layer was dried with magnesium sulfate ($MgSO_4$), and the ethyl acetate was distilled, thus obtaining 4.5 g of HMF (yield rate: 71%). As a result of an 1H-NMR analysis on the obtained 5-hydroxymethyl-2-furfural (HMF), it can seen that a high-purity 5-hydroxymethyl-2-furfural (HMF) was obtained as illustrated in FIG. 2.

In experiment example 1, in order to select the optimal solvent to be used for converting maize syrup containing fructose into 5-hydroxymethyl-2-furfural, different yield rates of 5-hydroxymethyl-2-furfural were compared obtained from applying different organic solvents. Accordingly, it could be seen that when dioxane was used as solvent, 79% of yield rate of 5-hydroxymethyl-2-furfural was obtained. This is an excellent result that is close to the 81% or more yield rate of 5-hydroxymethyl-2-furfural (HMF) obtained when using dimethylsulfoxide (DMSO), well known as the optimal solvent in conventional methods.

Furthermore, in experiment example 2, in order to obtain the optimal reacting time, different yield rates of 5-hydroxymethyl-2-furfural were compared obtained from applying different reacting times. And it could be seen that the yield rate of 5-hydroxymethyl-2-furfural was the highest when reacted for 3 hours.

In experiment example 3, different yield rates of 5-hydroxymethyl-2-furfural were compared obtained from applying different amounts of acid radical in the solid acid catalyst. According to the experiment, when the amount of solid acid catalyst decreases, the reacting time is delayed, but even with only 2 g of Amberlyst 15 resin (acid radicals inside the solid acid catalyst/fructose=0.19), almost 70% of yield rate of 5-hydroxymethyl-2-furfural could be obtained.

In experiment example 4, different yield rates of 5-hydroxymethyl-2-furfural were compared obtained from applying different concentrations of maize syrup containing fructose. According to the experiment, when the concentration of the high-fructose maize syrup increases, the reacting time is delayed, but even under a reaction condition of high concentration (concentration of fructose in the high-fructose maize syrup: 1.5M) where 42.9 g of high-fructose maize syrup was put into 100 mL of dioxane, almost 60% or more yield rate of 5-hydroxymethyl-2-furfural could be obtained within 7 hours.

In experiment example 5, different yield rates of 5-hydroxymethyl-2-furfural were compared obtained from applying different number of times of reusing the catalyst. As a result of an HPLC analysis on the yield rates of 5-hydroxymethyl-2-furfural obtained through reusing Amberlyst 15 resin, it could be seen that the activity of Amberylst 15 resin was sustainable, providing yield rates of 79 to 82%.

In experiment example 6, 5-hydroxymethyl-2-furfural was produced from maize syrup containing fructose by the overall method of the present disclosure.

INDUSTRIAL APPLICABILITY

Embodiments of the present invention provide a method for converting maize syrup containing fructose into 5-hydroxymethyl-2-furfural wherein dioxane, nonuniform solid acid catalyst and organic solvent can be reused, so that such a reaction can be performed continuously, thus enabling commercial mass production of 5-hydroxymethyl-2-furfural.

A number of examples have been described above. Nevertheless, it will be understood that various modifications may be made. For example, suitable results may be achieved if the described techniques are performed in a different order and/or if components in a described system, architecture, device, or circuit are combined in a different matter and/or replaced or supplemented by other components or their equivalents. Accordingly, other implementations are within the scope of the following claims.

What is claimed is:

1. A method for producing 5-hydroxymethyl-2-furfural (HMF) from maize syrup containing fructose,
   wherein the 5-hydroxymethyl-2-furfural is expressed by chemical formula:

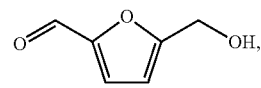

and
   the method comprises a conversion step in which a reactant containing the 5-hydroxymethyl-2-furfural is produced by mixing and heating the maize syrup, a dioxane solvent, and a solid acid catalyst, wherein the solid acid catalyst is a cation exchange resin.

2. The method according to claim 1,
   further comprising:
   a filtration step of filtering the solid acid catalyst from the reactant;
   a distillation step of distilling the dioxane from the reactant that underwent the filtration step; and
   a purification step of purifying the reactant that underwent the distillation step.

3. The method according to claim 1,
   wherein the maize syrup comprises 20 to 30 parts by weight of water for 100 parts by weight of carbohydrate.

4. The method according to claim 1,
   wherein the maize syrup comprises 40 to 95 parts by equivalent of fructrose for 100 parts by equivalent of carbohydrate.

5. The method according to claim 1,
   wherein the maize syrup is generated from maize that is a type of carbohydrate biomass by an isomerization reaction.

6. The method according to claim 1,
   wherein at the conversion step, the maize syrup constitutes 1 to 50 parts by weight for 100 parts by weight of dioxane.

7. The method according to claim 1,
   wherein the solid acid catalyst comprises 0.1 to 1 parts by equivalent of acid radical for 100 parts by equivalent of the fructose.

8. The method according to claim 1,
   wherein at the conversion step, conversion is performed at a temperature of 80 to 150° C.

9. The method according to claim 1,
   wherein at the conversion step, conversion takes 1 to 8 hours.

10. The method according to claim 2,
    wherein at the filtration step, the isolated solid acid catalyst is reused as catalyst at the conversion step.

11. The method according to claim 2,
wherein at the distillation step, the isolated dioxane is reused as solvent at the conversion step.

12. The method according to claim 2,
wherein at the purification step, the reactant that underwent the distillation step is separated into an organic solvent layer comprising the 5-hydroxymethyl-2-furfural and a water layer comprising byproducts, by adding organic solvent and water to the reactant.

13. The method according to claim 12, further comprising a recovery step,
wherein at the recovery step, the organic solvent layer is dried through a dehydration process and the organic solvent is distilled, and thus the 5-hydroxymethyl-2-furfural is obtained.

14. The method according to claim 13,
wherein the organic solvent is isolated and is reused at the purification step.

15. The method according to claim 5, wherein the isomerization reaction is at a pH of from 4 to 9.

* * * * *